United States Patent [19]

Weber

[11] Patent Number: 4,924,086

[45] Date of Patent: May 8, 1990

[54] OPTICAL SCANNING APPARATUS FOR DETECTING FAULTS ON A SURFACE

[75] Inventor: Klaus Weber, Königsbronn, Fed. Rep. of Germany

[73] Assignee: Erwin Sick GmbH Optik-Elektronik, Fed. Rep. of Germany

[21] Appl. No.: 264,230

[22] Filed: Oct. 28, 1988

[30] Foreign Application Priority Data

Nov. 5, 1987 [DE] Fed. Rep. of Germany ....... 3737631

[51] Int. Cl.⁵ ............................................. G01N 21/89
[52] U.S. Cl. .................................. 250/235; 250/572; 356/431
[58] Field of Search ............... 250/235, 236, 563, 572; 350/6.8; 356/430, 431, 237, 238

[56] References Cited

U.S. PATENT DOCUMENTS

| | | | |
|---|---|---|---|
| 4,025,796 | 5/1977 | Erdmann | 250/235 |
| 4,326,799 | 4/1982 | Keene et al. | 250/236 |
| 4,402,609 | 9/1983 | Fetzer et al. | 356/431 |
| 4,775,238 | 10/1988 | Weber | 250/563 |

Primary Examiner—Edward P. Westin
Attorney, Agent, or Firm—Townsend and Townsend

[57] ABSTRACT

An optical scanning apparatus for plane surfaces (13) having a laser light source (20), a light deflecting means (16) illuminated by the laser beam, a telecentric image forming element (15) and a light receiving means. Parallel to the scanning line (11) generated by the light deflecting means (16) and the telecentric image forming element (15) there is arranged, at the angle of regular reflection, an image forming retroreflector (12; 38,39) which forms an image of the light bead running along the scanning line (11) on itself.

12 Claims, 2 Drawing Sheets

OPTICAL SCANNING APPARATUS FOR DETECTING FAULTS ON A SURFACE

BACKGROUND OF THE INVENTION

The invention relates to an optical scanning apparatus for flat surfaces comprising a laser light source. A periodic light deflecting means such as a mirror wheel is illuminated by a laser beam. A telecentric optical scanning system which directs the laser beam, is periodically swept over a specific angular range by the light deflecting means. The light deflecting means is in the form of a scanning beam which is displaced parallel to itself, at an angle of incidence (other than zero) towards the flat surface. There, a light bead arises which periodically scans the flat surface along a scanning line. A light receiving means is provided for the light reflected from the region of the scanning line on the surface.

Such optical scanning apparatuses (for example, as described in German Offenlegungsschrift No. 35 04 019 corresponding to U.S. Pat. No. 4,775,238) are used for seeking faults at regular or specularly reflecting surfaces. Here it is necessary in order to detect faults with a small beam deviation to render the fluttering of the flat surface harmless during the signal recording, with such fluttering occurring in particular when the flat surface is the surface of a moving material, for example a web of sheet metal in a rolling mill.

However, it sometimes happens, with a specularly reflecting material web, that waves or corrugations extending perpendicular to the scanning line, are to be detected with the light receiving apparatus in addition to individual surface faults, i.e. waves or corrugations of which the crests and troughs also extend parallel to the scanning line.

An apparatus for amplifying the dependence of the angular changes of an optical emergent beam on the angular changes of the associated incident beam is known from German Auslegeschrift No. 20 42 508, corresponding to U.S. Pat. No. 3,771,850. The known apparatus has a first pivotable mirror which is arranged with its pivot axis in the front focal point of a first lens. A second lens is provided on the side of the first lens remote from the pivotable mirror with the front focal point of the second lens coinciding with the rear focal point of the first lens. A second mirror is arranged in the rear focal point of the second lens and is perpendicular to the common optical axis of the two lenses.

A parallel light beam emerging from the fixed front focal point of the first lens is thus imaged by the first lens depending on the angle of incidence along a line in the rear focal plane. The second lens then forms an image of each point of the common focal plane at its inverse point via the second plane mirror. The reflected parallel light beam which leaves the first lens then reaches the front focal point of the first lens at the inverse angle. If the first pivotable mirror is not perpendicular to the common optical axis of the two lenses then the angle of incidence of the parallel light beam on the first mirror can be increased in this manner.

SUMMARY OF THE INVENTION

The object underlying the invention is now to provide an optical scanning apparatus of the initially named kind. Faults which cause small beam deflection can be detected in webs, in particular webs with specularly reflecting surfaces having low scattering in reflection, without fluttering of the flat surface or corrugations or waves extending perpendicular to the scanning line disturbing this sensitive measurement. With the present invention, it is possible to additionally detect waves extending perpendicular to the scanning line with troughs and crests extending parallel thereto by means of the light receiving apparatus.

In order to satisfy this object the invention provides that an image forming retroreflector is present at the angle of regular reflection and forms an image of the light bead running along the scanning line, with the image being formed either on the light bead or in the close vicinity thereof.

Various types and arrangements of image forming retroreflectors are provided for by the present invention.

The invention thus provides image forming retroreflectors which form an image of the scanning light bead on the flat surface once again, whereupon the radiation emerging from this secondary light beam passes to the light receiving arrangement. While the retroreflector with the cylindrical mirror compensates for angular deviations of the material surface in the direction perpendicular to the scanning line the retroreflectors with spherical image forming elements produce a compensation of angular deviations in any desired direction. The compensation ensures that the beam emerging from the secondary light bead coincides precisely with the incident beam and is only oppositely directed thereto, irrespective of the angular deviation of the surface.

It is only beam deflections due to surface faults which have a smaller extent than the light bead which are not compensated for due to the image reversal in the backwardly reflected beam and which are detected by technical measuring techniques through the photoreceiver arrangement. It is expedient with the apparatus of the invention when a partially transmitting mirror is arranged in the beam path between the telecentric optical scanning system and the light deflecting means, preferably near the latter and deflects a part of the received light to a photoreceiver arrangement. This embodiment is necessary because the transmitted and received light pass through one another in the manner of an autocollimation beam path.

Advantageous embodiments of the subordinate claims are set forth in the further subordinate claims appended hereto.

The invention will now be described in the following by way of example only and with reference to the drawing in which are shown:

DETAILED DESCRIPTION OF THE PREFERRED EMBODIMENTS

Figure 1:
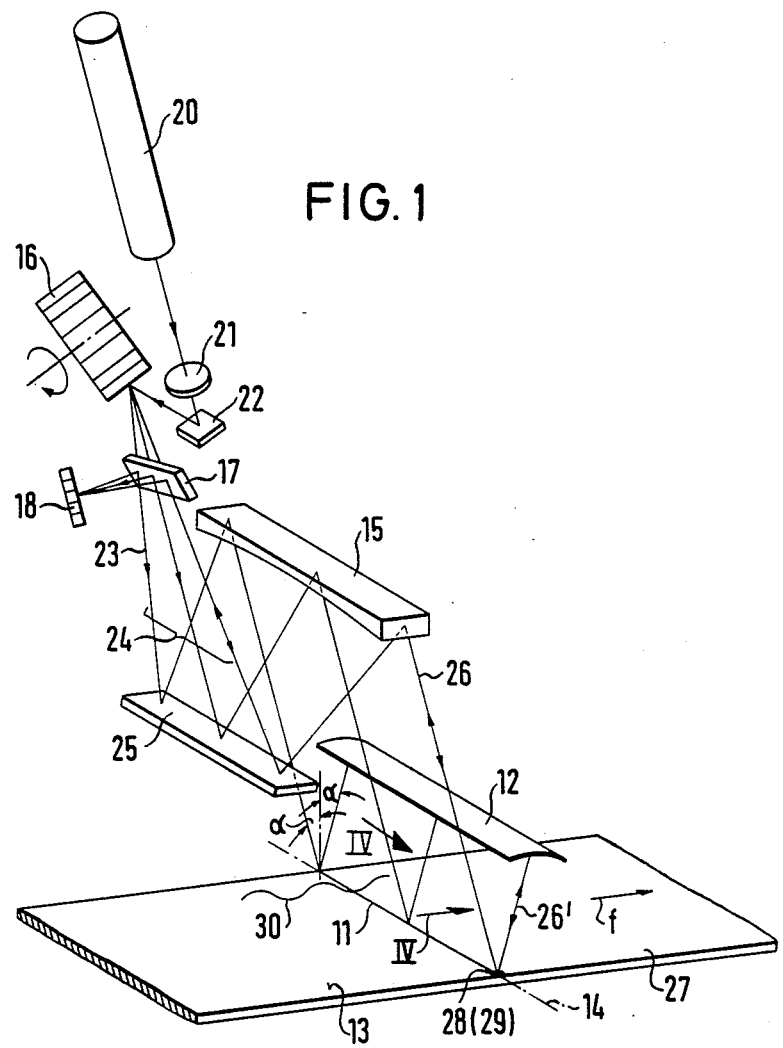
FIG. 1 is a schematic perspective illustration of a first embodiment of an optical scanning apparatus for flat surfaces in accordance with the invention.

In accordance with FIG. 1 a laser light source 20 illuminates a mirror wheel 16 via a beam broadening optical system 21, which is only schematically illustrated, and via a deflecting mirror 22. The mirror wheel reflects a sharply bundled light beam 23 which executes a periodic scanning movement within a sector-like region 24 in correspondence with the rotation of the mirror wheel in the direction of the arrow.

A strip-like plane mirror 25 reflects the light beam 23 executing the sector-like scanning movement to a strip-like concave mirror 15 which generates a scanning beam 26 which is displaced parallel to itself due to the fact that the concave mirror is arranged at a distance equal to its focal length from the reflecting surface of the mirror wheel 16.

The scanning beam 26 impinges on the flat surface 13 of a material web 27 which is for example moved in the direction of the arrow f beneath and through the described optical scanning apparatus, with the direction f extending perpendicular to the scanning line 11 along which the scanning beam 26 periodically sweeps transverse to the longitudinal direction of the material 27.

It is important that the transmitted scanning beam 26 does not extend perpendicular to the flat surface 13 but rather at an angle $\alpha$ of, for example, 15° to 45°. When the flat surface 13 is substantially specularly reflecting then the scanning beam 26 will be reflected at the reflection angle $\alpha$ as a deflected beam 26'. A right cylindrical mirror 12 is arranged, in accordance with the invention, in the path of the reflected beam 26' with the central axis 14 of the right cylindrical mirror coinciding with the scanning line 11. With normal reflection at the angle of reflection $\alpha$ the scanning beam falls on the central generatrix of the right cylindrical mirror 12, i.e. on the central surface line.

Figure 2:
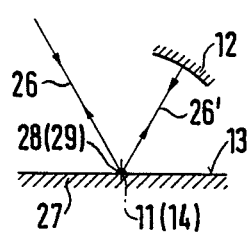
FIG. 2 is a schematic view of the scanning apparatus of FIG. 1 in the direction of the scanning line and parallel to the flat surface for the purpose of illustrating the manner of operation of the cylindrical mirror.

In accordance with FIGS. 1 and 2 the light which reaches the right cylindrical mirror 12 will, as a result of this arrangement, be reflected back on itself as from a retroreflector, so that a secondary light bead 29 will appear on the scanning line 11 in addition to the primary light bead 28 superimposed on the latter. Light will then be reflected back from the secondary light bead in alignment with the transmitted scanning beam 26 onto the strip-like concave mirror 15 and onto the plane deflecting mirror 25. A partially permeable mirror 17 is arranged close to the mirror wheel 16 in the transmission beam path and reflects out the light received from the secondary light bead to a linear photoreceiver array 18 which extends perpendicular to the scanning line 11. In this manner tilting of the material surface 13 about an axis parallel to the scanning line 11 or waves or corrugations 30 extending parallel to the scanning line 11 (of which one is shown by way of example in FIG. 1) do not influence the fault measurement. This is so since the light which is regularly reflected twice in the light bead, i.e. at precisely the same position on the surface 13 always coincides again with the transmitted scanning beam 26 irrespective of the degree of waviness.

If however the light bead impinges on a surface fault whose surface structure which deflects the beam is smaller than the light bead, then this beam deflection will not be compensated, since the beam forms the secondary light bead on its return path with elevation and side reversed, i.e. is reflected at different surface elements on the path to the material and on the path back to the material. The beam deflections which arise as a whole at the object point thus bring about scattering of the returning beam which is registered on the linear photoreceiver array 18.

Figure 3:
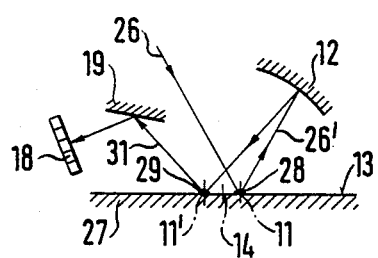
FIG. 3 is a view analogous to that of FIG. 2 of a further embodiment for wave measurement.

In accordance with FIG. 3, the right cylindrical mirror 12 is arranged tilted in such a way that the central axis 14 of the right cylinder lies somewhat alongside the scanning line of the transmitted scanning beam 26.

In this manner the reflex beam 26' reflected from the right cylindrical mirror 12 will impinge on the plane surface 13 to the side of the central axis 14 of the right cylindrical mirror and will there generate a secondary scanning light bead 29 which executes a scanning movement synchronous to the scanning light bead 28 along a secondary scanning line 11'. As a result of this arrangement the received light emerging from the secondary scanning line 11' will extend at a somewhat different angle from the transmitted scanning beam 26. Accordingly the secondary receiving light beam 31 can also fall onto a deflecting mirror 19 in the form of a plane mirror which is arranged alongside the transmitted light beam 26 and which again deflects the received light to a linear photoreceiver array 18.

In so far as different inclinations of a wave 30 (FIG. 1) are present at the location of the scanning light beads 28 and 29, the received light will fall on different positions of the photoreceiver array so that the degree of the waviness or corrugation can be determined from the electrical signals picked up from the photoreceiver array.

As a whole the photoreceiver array 18 indicates waves 30 extending in the longitudinal direction, with transversely extending wave crests and wave troughs. By displacement of the secondary light bead 29 generated on it in a frequency range equivalent to the scanning frequency and below, individual scattering faults are registered as an enlargement of this bead in frequency bands which are 100 to 1000 times higher.

Since the optical scanning apparatus described herein registers small scattering effects in reflection, it can also be combined with the customary receiver systems with cylindrical lens and light conducting rod with which faults which cause larger scattering are detected in the dark region adjacent the retroreflector. For example, light passing either side of the right cylindrical strip mirror 12 can be directed onto a light conducting rod via a cylindrical lens.

Figure 4:
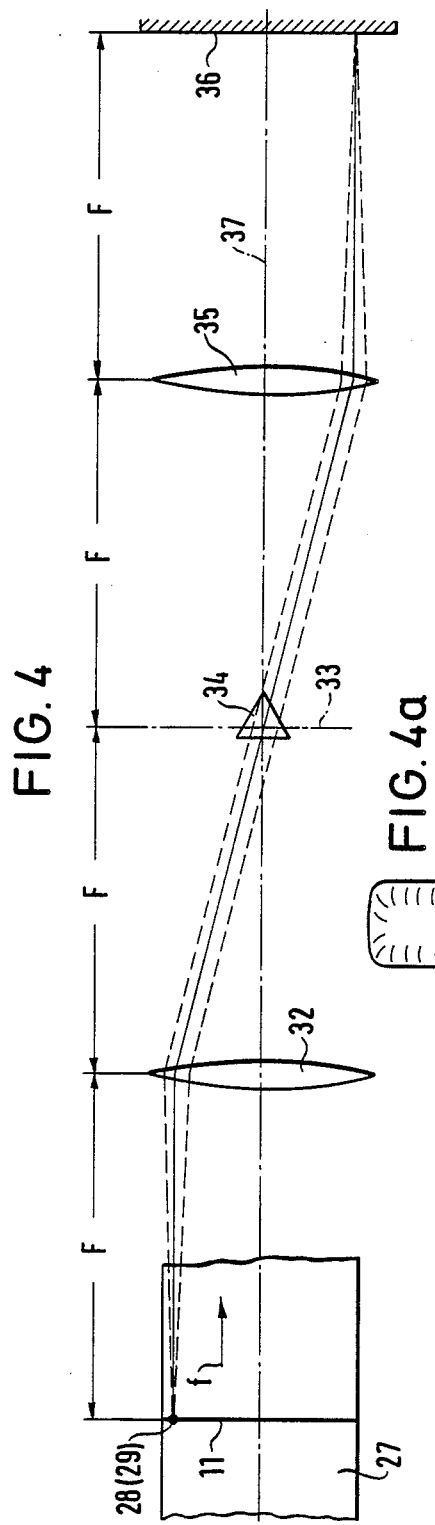
FIG. 4 is a view of two further embodiments of a reflection beam path in the direction of the arrow IV in FIG. 1.
Figure 4A:
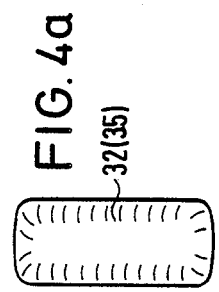
FIG. 4a is a plan view of the strip lenses used in the embodiments of FIGS. 4 and 5 (the plan view on the concave mirror strip used in FIG. 5 looks similar).

In the embodiment of the received beam path illustrated in FIG. 4 the light reflected from the scanning line 11 falls onto a lens strip 32 which is arranged parallel to the scanning line 11 at the distance of its focal length F therefrom. A triple mirror 34 is so arranged in the focal plane 33 remote from the scanning line 11 of the strip lens 32 on the optical axis 37 that it projects the incident light back in the same direction with slight lateral displacement so that it is projected by the lens strip 32 with a secondary light bead 29 onto the primary light bead.

Practically the same reflection light path can be achieved if, in place of the triple mirror 34, a further lens strip 35 is arranged at the distance F of its focal length from the focal plane 38, with a plane strip mirror 36 being located at the distance of the focal length F behind the further lens strip 35 and perpendicular to the optical axis 37. This embodiment however clearly takes up more space.

Figure 5:
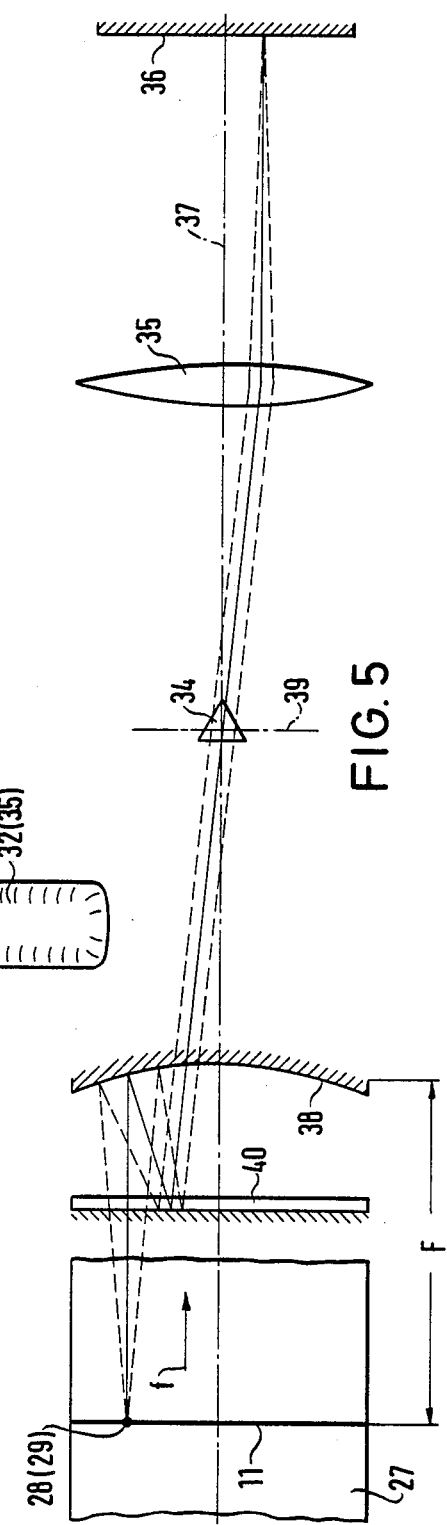
FIG. 5 is a view of two further embodiments of a reflection beam path in the direction of the arrow IV of FIG. 1.

In the first embodiment of FIG. 5 a concave mirror strip 38 is used in place of the strip lens 32 of FIG. 4. The concave mirror strip 38 is so arranged at the distance F of its focal length from the scanning line 11 that it receives the light reflected from there. The concave mirror strip 38 is so tilted about its longitudinal axis that a deflecting mirror strip 40 can be arranged alongside the incident beams for the concave mirror strip 38 with the deflecting mirror strip 40 receiving light reflected from the concave mirror strip 38 and deflecting it to the focal plane 39 of the concave mirror strip 38 which is displaced by the deflecting mirror strip 40 onto the side of the concave mirror strip 38 remote from the scanning line 11. There a triple mirror 34 is again arranged on the optical axis 37. The action is analogous to that of the first embodiment of FIG. 4. Also analogous to FIG. 4 one can again also provide a strip lens 35 behind the focal plane 39, with a mirror strip 36 arranged behind the strip lens 35 in place of the triple mirror 34. The second strip lens 35 could also be replaced in analogous manner by a concave mirror strip.

The embodiments of the reflection beam path of FIGS. 4 and 5 ensure that the primary light bead 28 is imaged back on itself as a secondary light bead 29.

In contrast to the cylindrical or channel mirror 12 of FIG. 1 the arrangement of spherical image forming elements of FIGS. 4 and 5 has the advantage that an image forming retroreflector is provided which compensates for angular fluctuations of the surface of the material web 27 both in and transverse to the scanning direction. With the image forming retroreflectors of FIGS. 4 and 5 both transverse and longitudinal waves are compensated in addition to these angular movements of the web.

For these arrangements an indication of the presence of the transverse longitudinal waves can be achieved if the secondary light bead is displaced transversely or along the scanning line ff, e.g. by slight tilting of the concave mirror 38 relative to the scanning line 11.

In the same way as one can use either spherical mirror strips or a telecentric scanning objective as the image forming elements at the transmission side this is also possible for the telecentric retroreflector of FIGS. 4 and 5.

What is claimed is:

1. Optical scanning apparatus for flat surfaces comprising:
   a laser light source;
   a periodic light deflecting means illuminated by a laser beam;
   a telecentric optical scanning system for directing the laser beam, periodically swept over a specific angular range by the light deflecting means in the form of a scanning beam displaced parallel to itself at an angle of incidence other than zero towards the flat surface where a light bead arises which periodically scans the flat surface along a scanning line;
   a light receiving means for receiving the light reflected from the region of the scanning line on the surface; and
   an image forming retroreflector disposed at an angle of regular reflection and forming an image of the light bead running along the scanning line, the image being formed adjacent the light bead.

2. Optical scanning apparatus in accordance with claim 1, wherein said image forming retroreflector comprises a right cylindrical mirror having substantially the length of the scanning line disposed at the angle of reflection of the scanning beam, an imaginary central cylindrical axis of the scanning beam extending parallel to the scanning line such that the imaginary central cylinder axis lies adjacent the scanning line on the surface.

3. Optical scanning apparatus in accordance with claim 1, wherein said image forming retroreflector comprises a spherical lens strip having substantially the length of the scanning line disposed at the angle of reflection of the scanning beam parallel to the scanning line and spaced from the scanning line by a distance equivalent to its focal length, said apparatus including a further lens strip extending parallel to the first lens strip disposed at the distance of its focal length from the focal plane of the first lens strip remote from the scanning line in such a way that it receives the reflected light emerging from the scanning line; and wherein a plane strip mirror is disposed behind the further lens strip perpendicular to the optical axis at a distance equal to the focal length of the further lens strip.

4. Optical scanning apparatus in accordance with claim 1, wherein said image forming retroreflector comprises a spherically concave mirror strip having substantially the length of the scanning line disposed at the angle of reflection of the scanning beam parallel to the scanning line and spaced from the scanning line by a distance equal to its focal length; wherein a focal plane of the concave mirror strip is displaced by a slight tilting of the concave mirror strip about its longitudinal axis, and further comprising a plane deflecting mirror strip disposed in the light reflected therefrom, onto a side of the concave mirror strip remote from the scanning line; and a further lens strip extending parallel to the first concave mirror strip disposed at a distance equal to its focal length, from the focal plane of the first concave mirror strip remote from the scanning line in such a way that it receives the reflected light emerging from the scanning line; and wherein a plane strip mirror is disposed behind the further lens strip, with the plane strip mirror being perpendicular to the optical axis and spaced behind the further lens strip by a distance equal to the focal length of the lens strip.

5. Optical scanning apparatus in accordance with claim 1, wherein said image forming retroreflector comprises a spherical concave mirror strip having substantially the length of the scanning line disposed at the angle of reflection of the scanning beam parallel to the scanning line at a distance from the scanning line equal to its focal length; and further comprising a triple mirror which receives the reflected light coming from the scanning line disposed in the focal plane of the concave mirror strip positioned remote from the scanning line due to slight tilting of the concave mirror about its longitudinal axis and due to a deflecting mirror strip arranged in the light reflected by the concave mirror strip.

6. Apparatus in accordance with claim 1, wherein said light receiving means comprises a photoreceiver arrangement and a partly permeable mirror disposed in a beam path between the telecentric optical scanning system and the light deflecting means and deflecting the light it receives from the surface to said photoreceiver arrangement.

7. Apparatus in accordance with claim 1, wherein the imaginary central cylindrical axis is arranged at a relatively small distance from the scanning line and parallel to the scanning line on the material surface.

8. Apparatus in accordance with claim 7, wherein the relatively small distance amounts to 5 to 10 mm.

9. Apparatus in accordance with claim 1, wherein the front focal point of the image forming retroreflector is spaced millimeters from the scanning line.

10. Apparatus in accordance with claim 1, wherein said light receiving means comprises a photoreceiver arrangement and a deflecting mirror disposed in a received beam path apart from the transmitted light beam adjacent to the light deflecting means and directs the light it receives from the surface to said photoreceiver arrangement.

11. Apparatus in accordance with claim 6, wherein the photoreceiver arrangement comprises a linear photoreceiver array extending perpendicular to the direction of the scanning line.

12. Apparatus in accordance with claim 10, wherein the photoreceiver arrangement comprises a linear photoreceiver array extending perpendicular to the direction of the scanning line.

* * * * *